United States Patent [19]

Nagata et al.

[11] Patent Number: 4,508,909

[45] Date of Patent: Apr. 2, 1985

[54] SYNTHESIS OF HYDROXYETHYLTETRAZOLETHIOL AND ETHERIFIED INTERMEDIATES THEREFOR

[75] Inventors: Wataru Nagata, Hyogo; Yasuhiro Nishitani, Osaka; Hisao Sato, Nara, all of Japan

[73] Assignee: Shionogi & Co., Ltd., Osaka, Japan

[21] Appl. No.: 475,410

[22] Filed: Mar. 15, 1983

[30] Foreign Application Priority Data

Mar. 24, 1982 [JP] Japan ................................. 57-47846

[51] Int. Cl.³ ........................................... C07D 257/04
[52] U.S. Cl. .................................................. 548/251
[58] Field of Search ......................................... 548/251

[56] References Cited

FOREIGN PATENT DOCUMENTS 51-68568  6/1976  Japan ................................. 548/251

Primary Examiner—Glennon H. Hollrah
Assistant Examiner—D. B. Springer
Attorney, Agent, or Firm—Birch, Stewart, Kolasch & Birch

[57] ABSTRACT

By heating an N-(2-hydroxyethyl)dithiocarbamate ester protected at its hydroxy group as an ether in the presence of an azide, the corresponding 1-(protected hydroxyethyl)-1H-tetrazole-5-thiol is obtained, and then, if required, deprotecting the etheric protection to give an industrially useful chemical, 1-(2-hydroxyethyl)-1H-tetrazole-5-thiol.

18 Claims, No Drawings

SYNTHESIS OF HYDROXYETHYLTETRAZOLETHIOL AND ETHERIFIED INTERMEDIATES THEREFOR

1. INTRODUCTION

This invention relates to an improved synthesis of 1-hydroxyethyl-1H-tetrazole-5-thiol or its mercaptide salt (III) which comprises heating an N-hydroxyethyldithiocarbamate ester protected at its hydroxy in the form of an ether (I) in the presence of an azide in an inert solvent and then deprotecting the produced corresponding 1-(protected hydroxyethyl)-1H-tetrazole-5-thiol or its mercaptide salt (II) according to the following scheme.

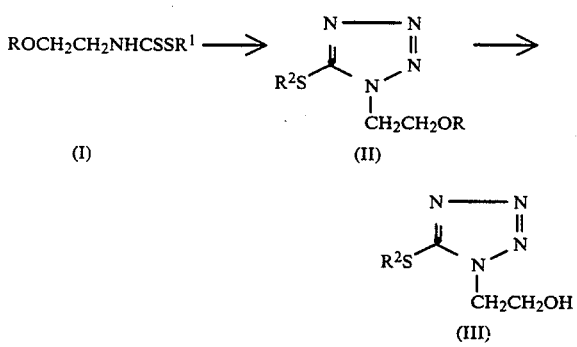

wherein
R is an ether forming group,
$R^1$ is an ester forming group and
$R^2$ is hydrogen or a salt forming atom or group.

2. BACKGROUND OF INVENTION

The objective compound of this invention (III) is already known e.g. by the specification of Japanese Patent Applications Kokai Nos. 51-68,568 and 52-33,692. However, when the examples of said patent literatures were traced by the present invention, the yield was found to be about 20 to 30%. They then sought several measures for improving the yield to find that when the hydroxyl group of the hydroxyethyldithiocarbamate is protected in an ether form, the yield was raised up to 90%. Based on this discovery, this invention was established.

3. STARTING MATERIALS

The starting material of the old process, N-(2-hydroxyethyl)-dithiocarbamic acid ester, is a known compound. However, the compound protected at its hydroxy as an ether (I) is a new compound. This form of protection protects the hydroxyethyl compounds from the basicity and reactivity of the azide in the reaction medium, and among them, more preferable protecting groups are those removable under a mild condition.

Representative ether forming groups suitable for the object of this invention and represented by R include linear, branched, cyclic or partly cyclic alkyl, aralkyl, aryl, heterocyclic, organosilyl and organostannyl groups. All of these can be unsaturated and/or substituted by a group inert to this reaction, e.g., $C_1$ to $C_3$-alkyl, alkoxy, aryl, halogen or nitro, and/or interrupted by a hetero atom selected from oxygen, nitrogen and sulfur in its nucleus, and containing 1 to 20 carbon atoms.

More preferable groups for R include an 2-oxaalicyclic group or alkyl optionally substituted at the 1 position with alkoxy or aryl. Further preferable groups for R are $C_4$ to $C_7$-tertiary alkyl, 1-$C_1$ to $C_6$-alkoxy-$C_1$ to $C_6$-alkyl, $C_4$ to $C_6$-2-oxacycloalkyl or triarylmethyl, and the most preferable R is a group selected from t-butyl, 1-ethoxyethyl, 1-isobutoxyethyl, 1-methoxy-1-methylethyl, tetrahydropyran-2-yl and trityl.

Preferable ester forming groups for $R^1$ are $C_1$ to $C_6$- (more preferably, $C_1$ to $C_3$)-alkyl.

The hydroxy group of the N-(2-hydroxyethyl)dithiocarbamate ester (II) can be protected in a conventional manner in the art for the specific protective group to be introduced, e.g., the addition to an olefin or condensation with a halide.

4. TETRAZOLE RING FORMATION

The tetrazole ring closure is carried out by heating the hydroxy-protected N-(2-hydroxyethyl)dithiocarbamic acid ester (I) in an inert solvent in the presence of an azide, e.g., an alkali metal or alkaline earth metal azide.

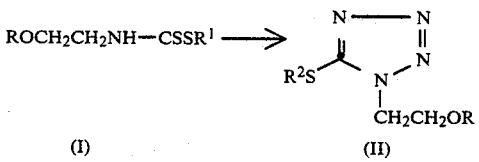

wherein R, $R^1$ and $R^2$ are as defined above. The inert solvent can be an aqueous solvent, e.g., $C_1$ to $C_4$-alkanol, $C_4$ to $C_6$-straight or cyclic ether or another industrial water-miscible solvent or mixture of these. The reaction is usually complete at a temperature between 30° C. and 150° C. in 0.5 to 10 hours.

The produced 1-(protected hydroxyethyl)-1H-tetrazole-5-thiol or its mercaptide salt (II) is a novel compound and can be isolated and purified in a manner conventional in the art, e.g., concentration, partition, extraction, washing, adsorption, elution, crystallization and/or drying. Preferable mercaptides for $R^2$ are alkali metal and alkaline earth metal atoms and are usually formed by a conventional mixing with a base.

5. DEPROTECTION

The deprotection of this intermediate (II) can be carried out in a manner conventional in the art for the removal of the protection group e.g., by the hydrolysis or elimination with an acid, e.g., Lewis acid, mineral acid, carboxylic acid, sulfonic acid, or for some groups, hydrogenolysis in the presence of a palladium or nickel catalyst, to give 1-(2-hydroxyethyl)-1H-tetrazole-5-thiol or its salt (III) according to the following scheme

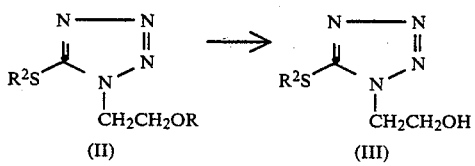

wherein R and $R^2$ are as defined above.

The deprotection can be done in an industrial inert solvent, preferably a polar solvent for the proton acid deprotection or a nonpolar solvent for the Lewis acid deprotection. Specific examples of these include water, a $C_1$ to $C_6$-alkanol, $C_3$ to $C_6$-straight or cyclic ether, $C_3$ to $C_6$-alkanone, $C_1$ to $C_6$-haloalkane or $C_6$ to $C_8$-aromatic hydrocarbon solvent or a mixture of these.

The deprotection is preferably carried out in an aqueous solvent at a pH between 0 to 4 with a mineral acid, carboxylic acid or sulfonic acid, or in an anhydrous solvent with a Lewis acid, both at a temperature between $-20°$ C. and $150°$ C. for a time between 5 minutes and 10 hours.

For 1 mole of the starting material, 0.4 to 10 molar equivalents of the reagent is usually used. The reaction can be carried out, if required, under an inert gas, e.g., nitrogen.

The reaction conditions given above for both of the tetrazole ring formation and deprotection show some preferable ranges, but are not to be taken as the critical ones.

6. TYPICAL REACTIONS

In a typical run, the dithiocarbamic acid alkyl ester (I) wherein R is tertiary butyl, 1-$C_1$ to $C_4$-alkoxy-$C_1$ to $C_3$-alkyl, tetrahydropyran-2-yl or triphenylmethyl and $R^1$ is $C_1$ to $C_3$-alkyl, is heated in the presence of 1 to 3 molar equivalents of an alkali metal azide in a mixture of 1 to 40 parts by weight of $C_1$ to $C_6$-alkanol or $C_4$ to $C_6$-dioxacycloalkane and 1 to 10 parts by weight of water at a temperature between $40°$ C. and $150°$ C. for a time between 35 and 330 minutes to form the alkali metal mercaptide salt of the compound (II) where $R^2$ is alkali metal. By a conventional work up, this affords the free thiol (II) where $R^2$ is hydrogen.

A typical deprotection is carried out by keeping 1-(protected hydroxyethyl)-1H-tetrazole-5-thiol (II) where R is tertiary butyl, 1-$C_1$ to $C_4$-alkoxy-$C_1$ to $C_3$-alkyl, tetrahydropyran-2-yl or triphenylmethyl and $R^2$ is hydrogen or alkali metal, at a pH between 0.5 to 4 in a mixture of 0 to 30 parts by weight of $C_1$ to $C_6$-alkanol, $C_3$ to $C_6$-alkanone or $C_4$ to $C_6$-dioxacycloalkane and 0 to 33 parts by weight of water at a temperature between $0°$ C. and $40°$ C. for a time between 5 and 330 minutes to form the free thiol compound (III) where $R^2$ is hydrogen.

Alternatively, the same starting material (II) is dissolved in a mixture of 0 to 20 parts by weight of $C_1$ to $C_6$-halohydrocarbon, 0.5 to 5 parts by weight of trifluoroacetic acid or 0.5 to 5 molar equivalents of aluminum or titanium chloride and 1 to 5 parts by weight of anisole, kept at a temperature between $-10°$ C. and $40°$ C. for a time between 5 minutes and 3 hours, and then concentrated to remove the volatile material and washed to remove the reagent and by-products to obtain the thiol compound (III) where $R^2$ is hydrogen.

7. USE OF THE PRODUCTS

The products thus prepared can be used as an elasticizer or starting material for preparing useful pharmaceuticals, e.g., cephalosporins, or agricultural chemicals.

8. NOVEL COMPOUNDS

The starting materials (I) and intermediates (II) are novel compounds represented by the following formula

ROCH$_2$CH$_2$NHCSSR$^1$ (I)

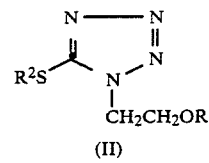

(II)

wherein R, $R^1$ and $R^2$ are as defined above.

A preferable R group is a 2-oxaalicyclic group or alkyl group optionally substituted at the 1 position with alkoxy or aryl; and a more preferable R group is $C_4$ to $C_7$-tertiary alkyl, triarylmethyl, 1-$C_1$ to $C_6$-alkoxy-$C_1$ to $C_6$-alkyl or $C_4$ to $C_7$-oxacycloalkan-2-yl. Some of the specific groups for R are t-butyl, 1-ethoxyethyl, 1-isobutoxyethyl, 1-methoxy-1-methylethyl, tetrahydropyran-2-yl and trityl. Preferable $R^1$ groups are methyl, ethyl or propyl. Preferable $R^2$ groups are alkali metal, e.g., lithium, sodium or potassium.

9. PREPARATION OF THE STARTING MATERIALS (I)

(Non-protected dithiocarbamate)

To a solution of ethanolamine (30.54 g) in a mixture of ethanol (370 ml) and water (30 ml) are added triethylamine (60.6 g) and carbon disulfide (45 g) at $15°$ C. After stirring for 1 hour, methyl iodide (80 g) is added thereto at $15°$ C. After 30 minutes' stirring, the reaction mixture is concentrated under reduced pressure, diluted with water (350 ml) and hexane, shaken and left to stand for a while to separate a water layer. The aqueous layer is acidified with phosphoric acid (1.5 ml), and extracted with ethyl acetate under salt-out condition. The extract is evaporated to remove the solvent to give N-(2-hydroxyethyl)dithiocarbamic acid methyl ester (81.7 g).

NMR(CDCl$_3$) $\delta$: 2.63(s, 3H), 2.73–3.08(m, 1H), 3.60–4.17(brs, 4H), 7.50–8.17(m, 1H).

(Protected dithiocarbamates)

(1) To a solution of N-(2-hydroxyethyl)dithiocarbamic acid methyl ester (7.5 g) in pyridine (40 ml) is added triphenylmethyl chloride (15 g), and the mixture is left to stand overnight at room temperature. The reaction mixture is poured into water and extracted with ethyl acetate. The extract is washed with diluted hydrochloric acid and water, dried and concentrated to remove the solvent. The residue is crystallized from a mixture of dichloromethane and ether to give N-(2-triphenylmethoxyethyl)dithiocarbamic acid methyl ester (14.73 g).

(2) In a sealed glass tube is placed a solution of N-(2-hydroxyethyl)dithiocarbamic acid methyl ester (4.3 g), isobutene (30 ml) and concentrated sulfuric acid (0.1 ml) in dichloromethane (20 ml) prepared at $-50°$ C. to $-60°$ C. The mixture is warmed slowly to room temperature and then left to stand for 17 hours. The reaction mixture is poured into aqueous 0.5% sodium hydroxide and extracted with dichloromethane. The extract is washed with water, dried and concentrated to give N-(2-t-butoxyethyl)dithiocarbamic acid methyl ester.

(3) To a solution of N-(2-hydroxyethyl)dithiocarbamic acid methyl ester (81.7 g) in dichloromethane (300 ml) are added dihydropyran (54 g) and toluene-p-sulfonic acid monohydrate (1.0 g), and the mixture is stirred for 1 hour. The reaction mixture is poured in aqueous sodium hydrogen carbonate, shaken and the resulting organic layer is separated. The layer is concentrated under reduced pressure to give N-[2-(2-tetrahydropyranyl)oxyethyl]dithiocarbamic acid methyl ester (129 g).

(4) To an ice cold and stirred mixture of N-(2-hydroxyethyl)dithiocarbamic acid methyl ester (1.513 g) and ethoxyethylene (1.92 ml) is added toluene-p-sulfonic acid monohydrate (9.5 mg). After stirring for 30 minutes at room temperature, the homogeneous solution is mixed with triethylamine (8 μl) and concentrated under reduced pressure to yield N-[2-(1-ethoxyethoxy)ethyl]-dithiocarbamic acid methyl ester (2.4 g).

(5) To a mixture of N-(2-hydroxyethyl)dithiocarbamic acid methyl ester (1.513 g) and isobutoxyethylene (2.59 ml) is added toluene-p-sulfonic acid monohydrate (9.5 mg). After stirring for 30 minutes, triethylamine (8 μl) is added to the mixture, and the resulting solution is concentrated under reduced pressure to give N-[2-(1-isobutoxyethyl)ethyl]dithiocarbamic acid methyl ester (3.2 g). Yield: 95%.

(6) To a mixture of N-(2-hydroxyethyl)dithiocarbamic acid methyl ester (1.513 g) and 2-methoxypropene (1.92 ml) is added toluene-p-sulfonic acid monohydrate (9.5 mg) at 10° C. After stirring for 1 hour, a trace amount of triethylamine is added and concentrated under reduced pressure to give N-[2-(2-methoxyisopropoxy)ethyl]dithiocarbamic acid methyl ester (2.78 g). Yield: 80%.

10. EXAMPLES

The following examples are given to illustrate embodiments of this invention.

In the following examples, the concentration is usually carried out under reduced pressure until the volatile solvent used is removed; and the drying is done with sodium sulfate or magnesium sulfate for the convenience of the laboratory use. The J-values in the NMR data show the coupling constants in Hz-values with an apparatus of 60 Mc.

EXAMPLE 1

(Tetrazole ring formation)

To a solution of N-(2-protected hydroxyethyl)dithiocarbamic acid methyl ester in a solvent is added a solution of sodium azide in water. After heating for the given time, the mixture is concentrated to remove the solvent, dissolved in water, washed with ethyl acetate, acidified with phosphoric acid and extracted with ethyl acetate. The extract is washed with water, dried and concentrated to give the corresponding 1-(2-protected hydroxyethyl)-1H-tetrazole-5-thiol.

The reaction conditions are given on Table I-1 and the physical constants of the products are given in Table II-2.

EXAMPLE 2

(Deprotection)

(1) A solution of 1-(2-protected hydroxyethyl)-1H-tetrazole-5-thiol in a solvent is acidified with an acid to the given pH and the mixture is kept at the given temperature for the given time. The reaction mixture is concentrated under reduced pressure. The obtained residue is extracted with ether, dried and concentrated. The residue is crystallized from a mixture of ethyl acetate and hexane to give 1-(2-hydroxyethyl)-1H-tetrazole-5-thiol. mp. 135°–137° C.

The reaction conditions are given in Table I-2.

EXAMPLE 3

(Deprotection)

To a solution of aluminum chloride (0.2 g) in anisole (1 ml) cooled at 0° C. is added a solution of 1-(2-t-butoxyethyl)-1H-tetrazole-5-thiol (0.202 g) in dichloromethane (2 ml), and the mixture is stirred at room temperature for 3 hours. The reaction mixture is poured into a mixture of 3N-hydrochloric acid (10 ml) and ethyl acetate (20 ml), shaken and the resulting organic layer is taken up. The layer is extracted with aqueous 5% sodium hydroxide. The extract is acidified with hydrochloric acid and extracted again with ethyl acetate. The extract is concentrated under reduced pressure to give 1-(2-hydroxyethyl)-1H-tetrazole-5-thiol. mp. 135°–136° C.

EXAMPLE 4

(Sodium salt)

A solution of 1-[2-(tetrahydropyran-2-yl)oxyethyl]-1H-tetrazole-5-thiol (23 g) in water (120 ml) containing sodium hydrogen carbonate (8.4 g) is concentrated under reduced pressure. The residue is crystallized from a mixture of ether and hexane to give 1-[2-(tetrahydropyran-2-yloxy)ethyl]-1H-tetrazole-5-thiol sodium salt (23.5 g). mp. 177°–180° C.

TABLE I-1

Reaction conditions of the tetrazole formation $$ROCH_2CH_2NHCSSCH_3 \longrightarrow$$

(I)    (II)

| No. | R | NaN$_3$ (mole) | solvent (amount) | H$_2$O (amt) | Time (min.) | Temperature (°C.) |
|---|---|---|---|---|---|---|
| 1 | t-C$_4$H$_9$— | 1.2 | C$_2$H$_5$OH 10 | 3.1 | 120 | refl. |
| 2 | t-C$_4$H$_9$— | 3.0 | dioxane 40 | 10 | 60 | 80 |
| 3 | CH$_3$<br>\|<br>C$_2$H$_5$OCH— | 1.3 | C$_2$H$_5$OH 6.7 | 3.3 | 80 | refl. |

TABLE I-1-continued

Reaction conditions of the tetrazole formation $$ROCH_2CH_2NHCSSCH_3 \longrightarrow \underset{(II)}{\underset{CH_2CH_2OR}{\text{tetrazole}}}$$

(I) → (II)

| No. | R | NaN$_3$ (mole) | solvent (amount) | H$_2$O (amt) | Time (min.) | Temperature (°C.) |
|---|---|---|---|---|---|---|
| 4 | CH$_3$–C$_2$H$_5$OCH— | 1.1 | CH$_3$OH 1.2 | 2.3 | 330 | 40 |
| 5 | CH$_3$–i-C$_4$H$_9$OCH— | 1.3 | C$_2$H$_5$OH 6.3 | 3.2 | 80 | refl. |
| 6 | CH$_3$OC(CH$_3$)$_2$— | 1.0 | C$_2$H$_5$OH 7.8 | 4.0 | 35 | refl. |
| 7 | (tetrahydropyranyl) | 1.2 | C$_2$H$_5$OH 2.6 | 1.7 | 150 | refl. |
| 8 | (C$_6$H$_5$)$_3$C— | 1.2 | C$_2$H$_5$OH 10.1 | 3.7 | 120 | refl. |

Note:
(a) The amount of the solvent and water is expressed by the weight ratio to the dithiocarbamate starting material.
(b) refl. shows heating under reflux.

TABLE I-2

Deprotections of the protected hydroxy.

(II) → (III)

| No. | R | Solvent (amt.) | Water (amt.) | pH | Temp. (°C.) | Time (min.) |
|---|---|---|---|---|---|---|
| 1 | CH$_3$–C$_2$H$_5$OCH— | CH$_3$COCH$_3$ 10 | 0.5 | 2 | 0 | 50 |
| 2 | CH$_3$–C$_2$H$_5$OCH— | C$_2$H$_5$OH 30 | 20 | 1 | 0 | 5 |
| 3 | CH$_3$–i-C$_4$H$_9$OCH— | CH$_3$COCH$_3$ 7 | 0.5 | 2 | 0 | 50 |
| 4 | CH$_3$OC(CH$_3$)$_2$— | — | 5 | 2 | rt | 10 |
| 5 | (tetrahydropyranyl) | CH$_3$COCH$_3$ 4.5 | 4 | 2 | rt | 120 |
| 6 | (tetrahydropyranyl) | dioxane 2 | 1 | 4 | 40 | 330 |

TABLE I-2-continued

Deprotections of the protected hydroxy.

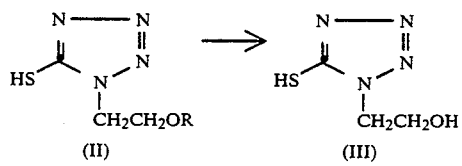

(II) → (III)

| No. | R | Solvent (amt.) | Water (amt.) | pH | Temp. (°C.) | Time (min.) |
|---|---|---|---|---|---|---|
| 7 | $(C_6H_5)_3C-$ | $CH_3OH$ 33 | 3 | 0.5 | rt | 300 |

Note:
1. The amount of the solvent and water is expressed by the weight ratio to the protected hydroxyethyltetrazolethiol.
2. rt shows room temperature.

TABLE II-1

Physical constants of the starting dithiocarbamic acid methyl esters, $ROCH_2CH_2NHCSSCH_3$ (I)

| No. | R | IR: $\nu_{max}^{CHCl_3}$ cm$^{-1}$ | NMR: $\delta_{ppm}^{CDCl_3}$ |
|---|---|---|---|
| 1 | $t\text{-}C_4H_9-$ | — | 1.2(s,9H), 2.63(s,3H), 3.55 (t,J = 4.5Hz,2H), 3.73–4.03 (m,2H). |
| 2 | $C_2H_5O\overset{\underset{\mid}{CH_3}}{C}H-$ | 3370, 3245. | 1.22(t,J = 7Hz,3H), 1.35(d, J = 5Hz,3H), 1.57(s,1H), 3.4–4.1 (m,4H), 4.69(q,J = 5Hz,1H). |
| 3 | $i\text{-}C_4H_9O\overset{\underset{\mid}{CH_3}}{C}H-$ | 3370, 3235. | 0.91(d,J = 7Hz,6H), 1.30(d,J = 5Hz, 3H), 1.52(s,1H), 1.6(m,1H), 2.64(s,3H), 3.1–4.1(m,6H), 4.68(q,J = 5Hz,1H). |
| 4 | $CH_3OC(CH_3)_2-$ | 3380, 3250, 1601. | 1.33(s,6H), 2.63(s,3H), 3.19 (s,3H), 3.63(t,J = 4Hz,2H), 3.89(t,J = 4Hz,2H). |
| 5 | 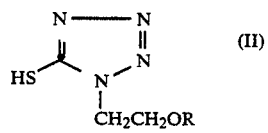 | 3360. | 1.33–2.00(m,6H), 2.63(s,3H), 3.47–4.17(s,6H), 4.33–4.67 (m,1H), 7.50–8.33(m,1H). |
| 6 | $(C_6H_5)_3C-$ | 3360. | 2.60(s,3H), 3.35(t,J = 5Hz,2H), 3.60–4.07(m,2H), 7.07–7.63 (m,16H). |

TABLE II-2

Physical constants of the 1-protected hydroxyethyltetrazole-5-thiols.

(II)

| No. | R | IR: $\nu_{max}^{CHCl_3}$ cm$^{-1}$ | NMR: $\delta_{ppm}^{CDCl_3}$ |
|---|---|---|---|
| 1 | $t\text{-}C_4H_9-$ | — | 1.3(s,9H), 3.87(t,J = 5.25Hz,2H), 4.47(t,J = 5.25Hz,2H), 11.87(s,1H). |
| 2 | $C_2H_5O\overset{\underset{\mid}{CH_3}}{C}H-$ | 3397. | 1.07(t,J = 7Hz,3H), 1.17(d,J = 6Hz, 3H), 3.40(q,J = 7Hz,2H), 3.98 (t,J = 5Hz,2H), 4.43(t,J = 5Hz,2H), 4.69(q,J = 6Hz,1H), 7.5(brs,1H). |
| 3 | $i\text{-}C_4H_9O\overset{\underset{\mid}{CH_3}}{C}H-$ | 3415. | 0.90(d,J = 6Hz,6H), 1.28(d,J = 6Hz, 3H), 1.82(m,1H), 3.20(m,2H), 4.00(t,J = 5Hz,2H), 4.52(t,J = 5Hz,2H), 4.75(q,J = 6Hz,1H), 10.0(brs, 1H). |
| 4 | $CH_3OC(CH_3)_2-$ | — | — |

TABLE II-2-continued
Physical constants of the 1-protected hydroxyethyltetrazole-5-thiols.

$$\underset{\underset{CH_2CH_2OR}{|}}{\underset{N}{\overset{N\text{———}N}{\underset{\|}{\overset{\|}{\underset{N}{\overset{N}{\bigwedge}}}}}}}\quad\text{(II)}$$

| No. | R | IR: $\nu_{max}^{CHCl_3}$ cm$^{-1}$ | NMR: $\delta_{ppm}^{CDCl_3}$ |
|---|---|---|---|
| 5 | 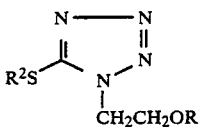 | — | 1.33–1.87(m,6H), 3.40–4.87(m, 7H), 12.57–13.16(m,1H). |
| 6 | $(C_6H_5)_3C$— | — | 3.50(t,J = 5Hz,2H), 4.45(t,J = 5Hz, 2H), 6.97–7.43(brs,15H)(CD$_3$COCD$_3$). |

What we claim is:

1. A process for preparing optionally protected 1-hydroxyethyl-1H-tetrazole-5-thiol or the mercaptide salt thereof which comprises the steps of heating an etherified N-hydroxyethyldithiocarbamate ester (I) in the presence of an azide in an inert solvent to give the corresponding etherified 1-(hydroxyethyl)-1H-tetrazole-5-thiol or the mercaptide salt thereof (II) and then, if required, removing the ether-forming group to give the free alcohol compound (III), the compounds I, (II) and (III) having the following formulae:

$$ROCH_2CH_2NHCSSR^1 \quad \text{(I)}$$

$$\underset{\underset{CH_2CH_2OR}{|}}{\underset{N}{\overset{N\text{———}N}{\underset{\|}{\overset{\|}{\underset{N}{\overset{N}{\bigwedge}}}}}}}R^2S\quad\text{(II)}$$

$$\underset{\underset{CH_2CH_2OH}{|}}{\underset{N}{\overset{N\text{———}N}{\underset{\|}{\overset{\|}{\underset{N}{\overset{N}{\bigwedge}}}}}}}R^2S\quad\text{(III)}$$

wherein R is an ether forming group selected from the group consisting of tertiary alkyl, triarylmethyl, 1-($C_1$ to $C_6$-alkoxy)-$C_1$ to $C_6$-alkyl and $C_4$ to $C_6$-2-oxacycloalk-1-yl, $R^1$ is an ester forming group and $R^2$ is hydrogen or an alkali metal or alkaline earth metal salt forming group.

2. A process as claimed in claim 1 wherein R is $C_4$ to $C_7$-tertiary alkyl.

3. A process as claimed in claim 1 wherein R is triarylmethyl.

4. A process as claimed in claim 1 wherein R is a group selected from t-butyl, 1-ethoxyethyl, 1-isobutoxyethyl, 1-methoxy-1-methylethyl, tetrahydropyran-2-yl and trityl.

5. A process as claimed in claim 1 wherein $R^1$ is $C_1$ to $C_6$-alkyl.

6. A process claimed in claim 1 wherein the azide is an alkali metal or alkaline earth metal azide.

7. A process as claimed in claim 1 wherein the mercaptide salt $R^2$ is an alkali metal or alkaline earth metal salt.

8. A process as claimed in claim 1 wherein the inert solvent is an aqueous solvent.

9. A process as claimed in claim 1 wherein the heating is conducted to keep the medium at a temperature between 30° C. and 150° C. for a time between 0.5 and 10 hours.

10. A process as claimed in claim 1 wherein the removal of the ether-forming group is carried out in an aqueous medium at a pH between 0 to 4 with a mineral acid, carboxylic acid or sulfonic acid.

11. A process as claimed in claim 1 wherein the removal of the ether-forming group is carried out in an anhydrous medium with a Lewis acid.

12. A process as claimed in claim 1 wherein the removal of the ether-forming group is carried out at a temperature between −20° C. and 150° C. for a time between 5 minutes and 10 hours.

13. A process as claimed in claim 1 wherein R is tertiary butyl, 1-($C_1$ to $C_4$-alkoxy)-$C_1$ to $C_3$-alkyl, tetrahydropyran-2-yl or triphenylmethyl and $R^1$ is $C_1$ to $C_3$-alkyl, which comprises heating the corresponding dithiocarbamate ester (I) in the presence of 1 to 3 molar equivalents of the alkali metal azide in a mixture of 1 to 40 parts by weight of a $C_1$ to $C_6$-alkanol or $C_4$ to $C_6$-dioxacycloalkane and 0 to 10 parts by weight of water at a temperature between 40° C. and 150° C. for a time between 35 and 330 minutes.

14. A process as claimed in claim 1 wherein R is tertiary butyl, 1-$C_1$ to $C_4$-alkoxy-$C_1$ to $C_3$-alkyl, tetrahydropyran-2-yl or triarylmethyl and $R^1$ is $C_1$ to $C_3$-alkyl, which comprises maintaining the 1-(etherified hydroxyethyl)-1H-tetrazole-5-thiol or its alkali metal salt at a pH between 0.5 and 4 in a mixture of 0 to 30 parts by weight of $C_1$ to $C_6$-alkanol, $C_3$ to $C_6$-alkanone or $C_4$ to $C_6$-dioxacycloalkane and 1 to 33 parts by weight of water at a temperature between 0° C. and 40° C. for a time between 5 and 330 minutes.

15. A process as claimed in claim 1 wherein R is tertiary butyl, 1-$C_1$ to $C_4$-alkoxy-$C_1$ to $C_3$-alkyl, tetrahydropyran-2-yl or triarylmethyl and $R^1$ is $C_1$ to $C_3$-alkyl, which comprises maintaining the 1-(etherified hydroxyethyl)-1H-tetrazole-5-thiol at a temperature between −10° C. and 40° C. in a mixture of 0 to 20 parts by weight of $C_1$ to $C_6$-halohydrocarbon, 0.5 to 5 parts by weight of trifluoroacetic acid or 0.5 to 5 molar equivalents of aluminum or titanium chloride and 1 to 5 parts by weight of anisole for a time between 5 minutes and 3 hours.

16. A process as claimed in claim 1, wherein $R^1$ is $C_1$ to $C_3$-alkyl.

17. An N-(etherified hydroxyethyl)dithiocarbamic acid alkyl ester or 1-(etherified hydroxyethyl)-1H-tetrazole-5-thiol compound represented by the following formula

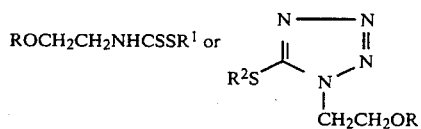

wherein R is an ether forming group,
$R^1$ is alkyl and
$R^2$ is hydrogen or alkali metal.

18. A compound as claimed in claim 17 wherein R is $C_4$ to $C_7$-tertiary alkyl, 1-($C_1$ to $C_6$-alkoxy)-$C_1$ to $C_6$-alkyl, $C_4$ to $C_6$-oxacycloalkan-2-yl or triarylmethyl, $R^1$ is methyl, ethyl, propyl or isopropyl, and $R^2$ is lithium, sodium or potassium.

* * * * *